US010364902B2

United States Patent
Moeller et al.

(10) Patent No.: US 10,364,902 B2
(45) Date of Patent: Jul. 30, 2019

(54) ROTARY SHEAR VALVE WITH A TWO-PIN DRIVE SHAFT FOR LIQUID CHROMATOGRAPHY APPLICATIONS

(75) Inventors: Mark W. Moeller, Kingston, MA (US); Robert A. Jencks, Mendon, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 350 days.

(21) Appl. No.: 14/117,397

(22) PCT Filed: Jun. 11, 2012

(86) PCT No.: PCT/US2012/041821
§ 371 (c)(1),
(2), (4) Date: Nov. 13, 2013

(87) PCT Pub. No.: WO2012/173908
PCT Pub. Date: Dec. 20, 2012

(65) Prior Publication Data
US 2014/0191146 A1 Jul. 10, 2014

Related U.S. Application Data

(60) Provisional application No. 61/497,986, filed on Jun. 17, 2011.

(51) Int. Cl.
*F16K 5/00* (2006.01)
*G01N 30/20* (2006.01)
*F16K 11/074* (2006.01)

(52) U.S. Cl.
CPC ............ *F16K 5/00* (2013.01); *F16K 11/0743* (2013.01); *G01N 2030/202* (2013.01)

(58) Field of Classification Search
CPC . F16K 5/00; F16K 11/0743; G01N 2030/202; Y10T 137/86863
See application file for complete search history.

(56) References Cited

U.S. PATENT DOCUMENTS

| 2,796,151 A * | 6/1957 | Bachman ............... B61H 11/14 |
| | | 188/204 R |
| 4,008,980 A * | 2/1977 | Noehren ................. B64C 27/33 |
| | | 416/134 A |

(Continued)

FOREIGN PATENT DOCUMENTS

| JP | WO 2009078450 A1 * | 6/2009 | ............... F16K 1/02 |
| JP | WO 2009101695 A1 * | 8/2009 | ......... F16K 11/0743 |

(Continued)

OTHER PUBLICATIONS

International Preliminary Report on Patentability for international patent application No. PCT/US12/41821, dated Jan. 3, 2014; 6 pages.

*Primary Examiner* — Marina A Tietjen
*Assistant Examiner* — Frederick D Soski
(74) *Attorney, Agent, or Firm* — Schmeiser, Olsen & Watts LLP

(57) ABSTRACT

A rotary shear valve assembly for liquid chromatography applications comprises a rotor assembly having a rotor and a drive shaft with a head portion. The rotor has a substantially planar surface with one or more rotor grooves and a pair of holes. The head portion has two pins. The pins are disposed substantially diametrically opposite of each other on a line through a center of the head portion. Each pin mates with one of the holes in the rotor. The rotor assembly can further comprise means for urging the rotor surface against the stator surface such that each rotor groove aligns with and provides a fluidic channel between two of the stator openings.

13 Claims, 10 Drawing Sheets

(56) References Cited

U.S. PATENT DOCUMENTS

| | | | | |
|---|---|---|---|---|
| 4,298,318 A | * | 11/1981 | Tsuchiya | F01C 1/104 |
| | | | | 137/625.21 |
| 4,444,066 A | | 4/1984 | Ogle et al. | |
| 4,619,640 A | * | 10/1986 | Potolsky | A61M 39/10 |
| | | | | 128/912 |
| 4,721,972 A | * | 1/1988 | Wakabayashi | G02B 7/08 |
| | | | | 396/349 |
| 4,971,535 A | * | 11/1990 | Okada | F04C 15/0023 |
| | | | | 418/133 |
| 5,161,507 A | | 11/1992 | Terazawa et al. | |
| 5,460,494 A | * | 10/1995 | Lee | F01C 17/06 |
| | | | | 418/14 |
| 5,462,085 A | * | 10/1995 | Iwata | F16K 11/074 |
| | | | | 137/614.21 |
| 5,920,006 A | * | 7/1999 | Zelechonok | F04B 7/0007 |
| | | | | 73/61.55 |
| 6,000,906 A | * | 12/1999 | Draskovich | F01D 5/3084 |
| | | | | 415/189 |
| 6,491,063 B1 | * | 12/2002 | Benatav | F25B 41/046 |
| | | | | 137/625.43 |
| 6,840,701 B2 | | 1/2005 | Dacunha et al. | |
| 2002/0002099 A1 | * | 1/2002 | Hara | F02B 63/04 |
| | | | | 477/5 |
| 2005/0199299 A1 | * | 9/2005 | Schick | F16K 11/074 |
| | | | | 137/625.46 |
| 2006/0034720 A1 | * | 2/2006 | Lee | F04C 18/3564 |
| | | | | 418/29 |
| 2009/0014078 A1 | * | 1/2009 | Gamache | F16K 7/12 |
| | | | | 137/625.48 |
| 2009/0050212 A1 | | 2/2009 | Dourdeville et al. | |
| 2010/0043019 A1 | * | 2/2010 | Kobayashi | G11B 23/0307 |
| | | | | 720/710 |
| 2011/0006237 A1 | | 1/2011 | Tower | |

FOREIGN PATENT DOCUMENTS

| | | | |
|---|---|---|---|
| WO | 2010051297 A1 | 5/2010 | |
| WO | WO 2010063125 A1 * | 6/2010 | G01N 30/20 |

* cited by examiner

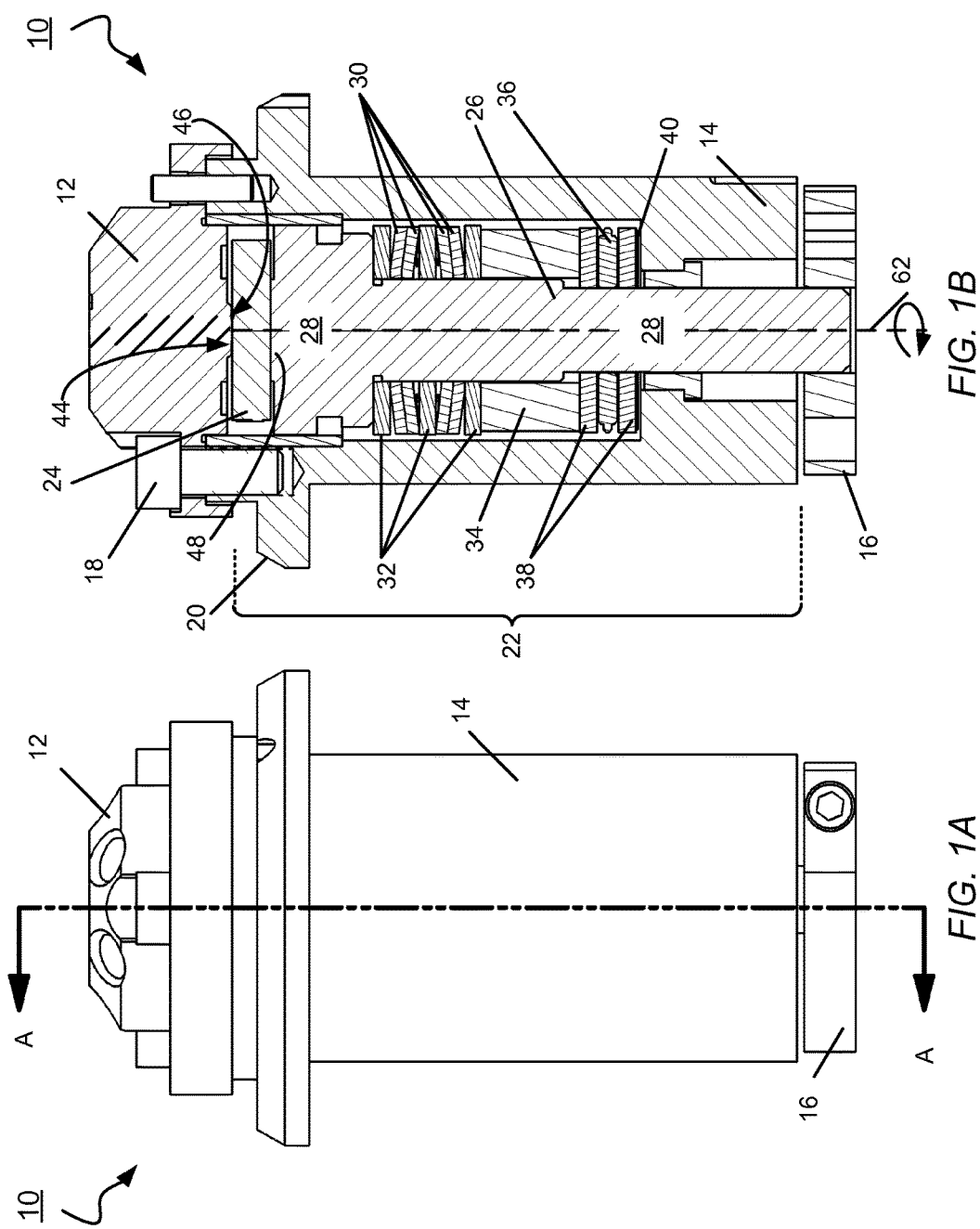

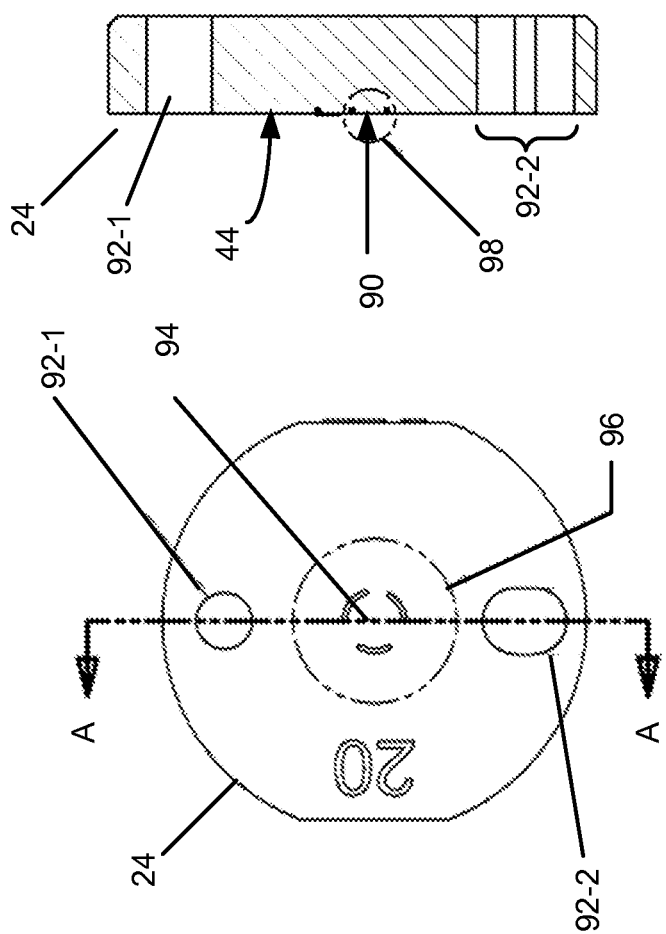
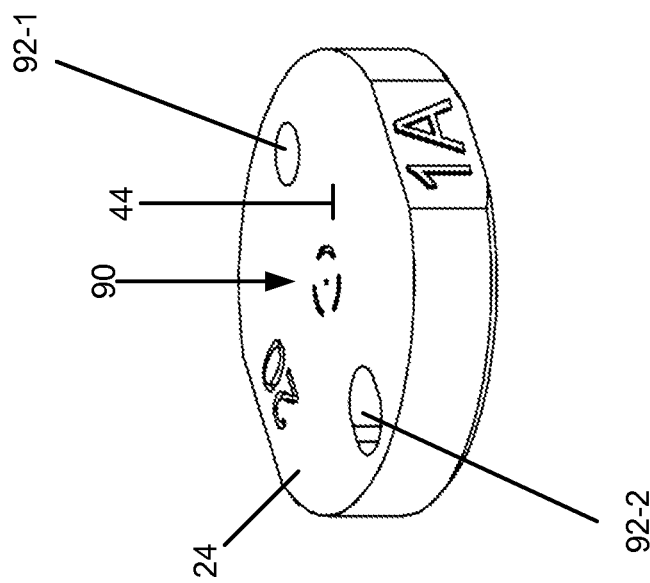
FIG. 4A  FIG. 4B  FIG. 4C

ROTARY SHEAR VALVE WITH A TWO-PIN DRIVE SHAFT FOR LIQUID CHROMATOGRAPHY APPLICATIONS

RELATED APPLICATION

This application claims the benefit of U.S. Provisional Patent Application No. 61/497,986 filed on Jun. 17, 2011, titled "Rotary Shear Valve with a Two-Pin", the entirety of which is incorporated by reference herein.

FIELD OF THE INVENTION

The invention relates generally to valve assemblies for switching pressurized fluids. More particularly, the invention relates to rotary shear valve assemblies for liquid chromatography applications.

BACKGROUND

High-pressure liquid chromatography systems, such as high performance liquid chromatography (HPLC) and ultra performance liquid chromatography (UPLC) systems, typically employ injection valves having a rotary shear seal. A force of several hundreds of pounds or more is applied between the rotor and stator to seal against pressures that can exceed 15,000 psi. The force is maintained while the rotor rotates between valve switch positions, thereby placing stringent requirements on the quality of the sealing surfaces. The injection valves are typically designed for tens of thousands of cycles without excessive wear and leakage. Liquid chromatography instrument manufacturers anticipate future instruments will require sealing pressures of injection valves to exceed 18,000 psi and still provide tens of thousands of cycles. The trend to greater operating pressures may be beyond the capabilities of design and materials of conventional injection valves. Increasing the compressive load may suffice to achieve higher sealing pressures, but this approach can result in faster wear of the rotor and stator, with an associated increased leakage and reduced valve lifetime.

SUMMARY

In one aspect, the invention features a rotary shear valve assembly comprising a rotor assembly having a rotor and a drive shaft with a head portion. The rotor has a substantially planar surface with one or more rotor grooves and a pair of holes. The head portion has two pins. The pins are disposed substantially diametrically opposite of each other on a line through a center of the head portion. Each pin mates with one of the holes in the rotor.

In another aspect, the invention features a rotary shear valve assembly comprising a rotor assembly having a drive shaft and a rotor. The drive shaft has a head portion with only two pins extending orthogonally from a distal surface of the head portion. The rotor has a substantially planar surface with one or more rotor grooves, a first hole for tightly receiving one of the two pins of the head portion, and a slot for receiving the other of the two pins.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 1A and FIG. 1B are side and a cross-sectional views, respectively, of an embodiment of a rotary shear valve assembly comprising a stator, housing for a rotor assembly, and drive shaft clamp.

FIG. 4A is an isometric view of an embodiment of the rotor.

FIG. 4B is a top view of the rotor.

FIG. 4C is a section view of the rotor in accordance with line A-A in FIG. 4B.

DETAILED DESCRIPTION

Rotary shear valve assemblies described herein have a two-pin drive shaft for holding a rotor in relation to a stator. The two pins of the drive shaft bear the driving force used to rotate the rotor under a compressive load. To couple to the drive shaft, the rotor has a mating hole and a slot for receiving the two pins of the drive shaft. The size of the mating hole is designed to closely receive one of the pins of the drive shaft, whereas the slot provides sufficient clearance in one dimension to facilitate the process of slipping the rotor over the pins of the drive shaft.

Having only two drive shaft pins has advantages over conventional three-pin shafts by achieving better alignment of the rotor to the stator through tighter tolerances and by providing a truer "on center" rotation force through the rotor. Having two pins, instead of three, produces less tolerance stack-up error for positioning the rotor to the stator, there being fewer critical dimensions that can contribute to the position error, and permits less clearance between one pin of the drive shaft and the rotor's mating hole. The reduced position error improves alignment between the rotor and stator, leading to less fluidic carryover, flow restriction, and dispersion. Having two pins also enables those driving forces acting on the pins to be diametrically opposed, producing a truer rotation effect of the rotor around the axis of the drive shaft and, consequently, prolonging valve life because of a more uniform wear of the rotor and stator than what is presently produced by three-pin drive shafts.

Figure 1C:
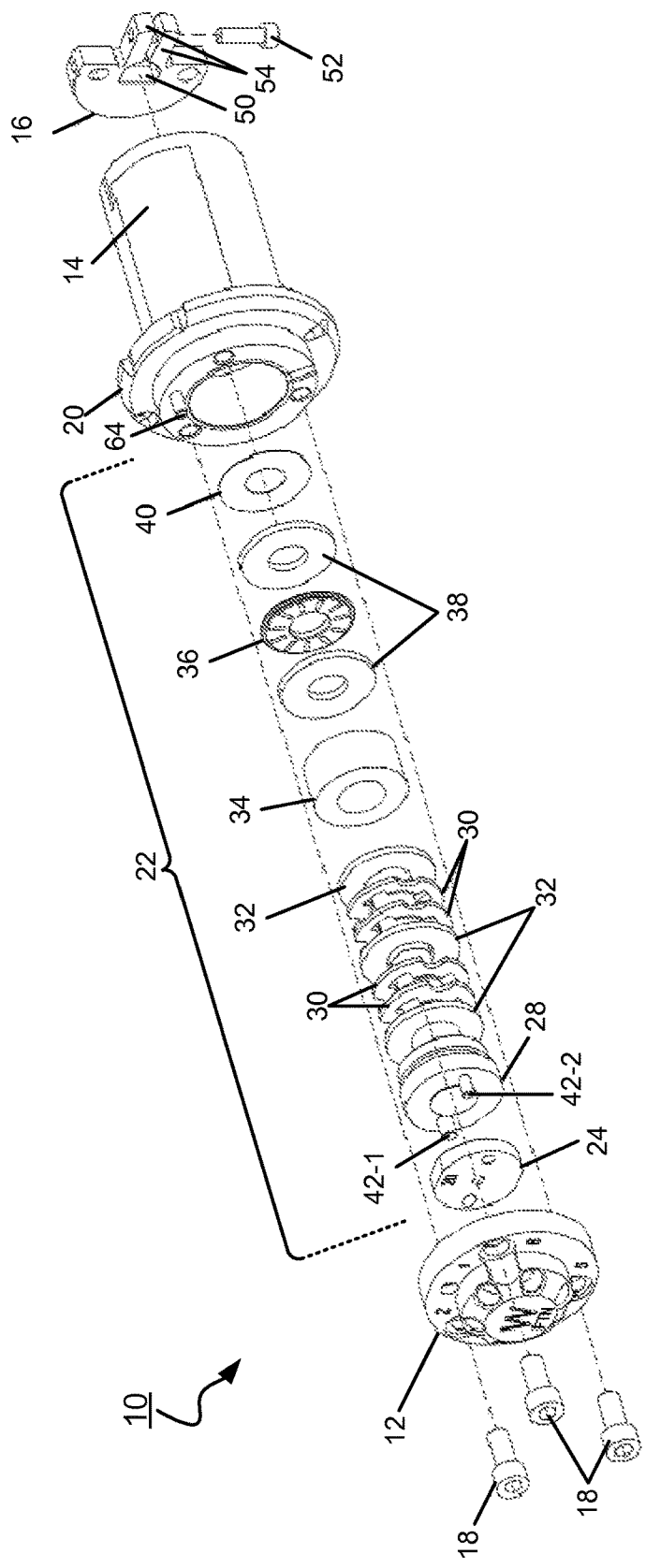
FIG. 1C is an exploded view of the rotary shear valve assembly.
Figure 1D:
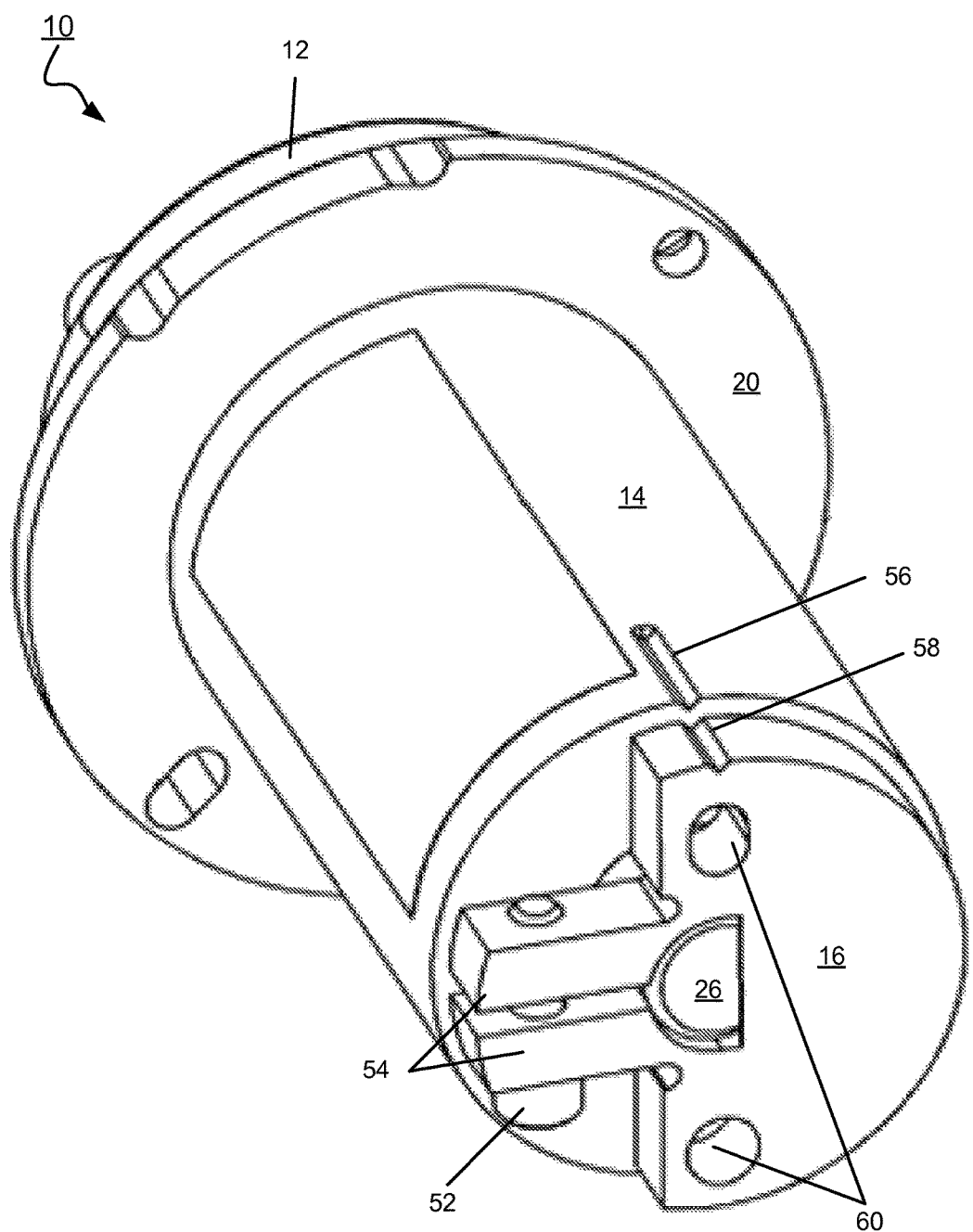
FIG. 1D is an isometric view the rotary shear valve assembly from the end with the drive shaft clamp.

FIG. 1A shows a side view of an embodiment of a rotary shear valve assembly 10 including a stator 12 secured to one end of a housing 14 and a drive shaft clamp 16 at the opposite end of the housing 14. FIG. 1B shows a cross-sectional view of the rotary shear valve assembly 10 taken along line A-A in FIG. 1A, FIG. 1C shows an exploded view of the rotary shear valve assembly 10, and FIG. 1D shows the rotary shear valve assembly 10 from the end with the drive shaft clamp 16. Mounting screws 18 secure the stator 12 to a flange 20 of the housing 14. The housing 14 substantially encloses a rotor assembly 22 comprised of a disk-shaped rotor 24, a drive shaft 26 with a head portion 28, four springs 30 grouped in two sets of two separated and flanked by washers 32, a spacer 34, a thrust bearing 36 sandwiched between bearing washers 38, and, optionally, a shim 40.

The rotor 24 is coupled to the head portion 28 of the rotor assembly 22. Extending orthogonally from the distal face of the head portion 28 are two pins 42-1, 42-2 that enter corresponding openings (FIG. 4A) in the rotor 24. A substantially planar surface 44 of the rotor 24 abuts an opposing surface 46 of the stator 12. In addition, the rotor 24 sits on a raised region or dais 48 of the head portion 28. The dais 48 concentrates the force applied to the rotor and is preferably smaller than the base surface of the rotor 24, so that the rotor 24 may slightly teeter on the dais 48 to facilitate complete contact between the rotor and stator surfaces 44, 46. In various embodiments, the rotor surface 44 is made of a PEEK or carbon-reinforced PEEK material and the stator surface 46 is made of a metallic material coated with a layer of DLC (Diamond-like Carbon) that dramatically reduces the friction between the stator and rotor surfaces. These combinations of materials have been demonstrated to achieve effective sealing for tens of thousands of cycles of valve rotation.

The drive shaft 26 extends through an opening at the base of the housing 14. The end of the drive shaft 26 extends into an opening 50 of the drive shaft clamp 16, which is appropriately shaped to closely receive a notched end (FIG. 3A) of the drive shaft. The end of the drive shaft 26 has a notch. A threaded screw 52 passes through pincers 54, which tightens the opening 50 about the drive shaft's end to hold the drive shaft 26 securely. When secured properly, the end of the drive shaft 26 is almost flush with the plane of the clamp 16. Alignment grooves 56, 58 on the housing 14 and clamp 16, respectively, are used to position these units appropriately for coupling the clamp 16 to the draft shaft 26. A drive mechanism (not shown) couples to holes 60 in the clamp 16 in order to provide a rotating force about a central axis 62 (FIG. 1B).

The compression of the springs 30 translates to an axial force to the rotor 24, urging the rotor surface 44 against the stator surface 46 and maintaining a fluidic seal at the interface of these surfaces 44, 46. In one embodiment, the springs 30 are clover springs. Other types of springs can be used, for example, Belleville washers, without departing from the principles described herein. In one embodiment, the compressive load achieved by the springs 30 is approximately 600 lbs. and is designed to produce a seal between the rotor and stator that can prevent leakage at fluidic pressures at least as great as 20,000 psi. For example, in UPLC instruments, the fluidic pressure typically ranges between 15,000 psi and 20,000 psi. The springs 30 maintain the applied force applied throughout the rotation of the drive shaft 26 and the rotor 24.

The spacer 34 serves to separate the thrust bearing 36 and bearing washers 38 from the spring stack comprised of the springs 30 and spring washers 32. The thrust bearing 36 and bearing washers 38 facilitate rotation of the drive shaft. The shim 40 is used to achieve the desired amount of compression along the axis of the draft shaft, with additional shims being added to the drive shaft until the compressive load produced by the springs 30 reaches the desired target of, for example, approximately 600 lbs.

Figure 2:
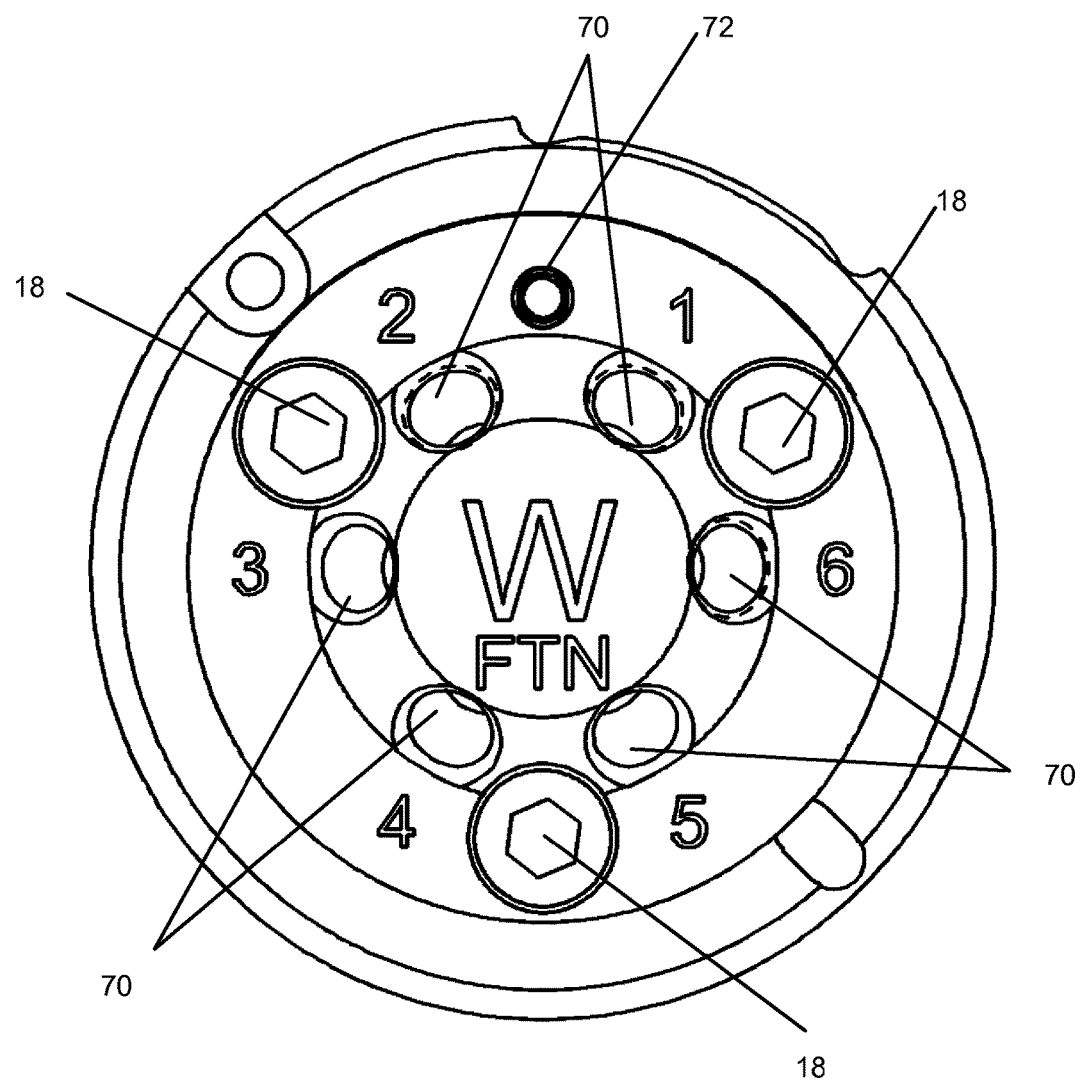
FIG. 2 is a view of the rotary shear valve assembly from the end with the stator.

FIG. 2 shows a top view of the rotary shear valve assembly 10 from the end with the stator 12. The stator 12 has six ports 70, each extending to an opening at the contact surface 46 of the stator. Each port 70 couples to a fluidic tube or channel (not shown), by which fluid flows to or from the rotary shear valve assembly 10. Rotation of the rotor 24 with respect to the stator 12 changes the connectivity of the ports 70, as described in more detail below. The stator 12 also has a guide hole 72 for receiving an alignment pin 64 (FIG. 1C) extending from the leading raised ring of the housing 14.

Figure 3A:
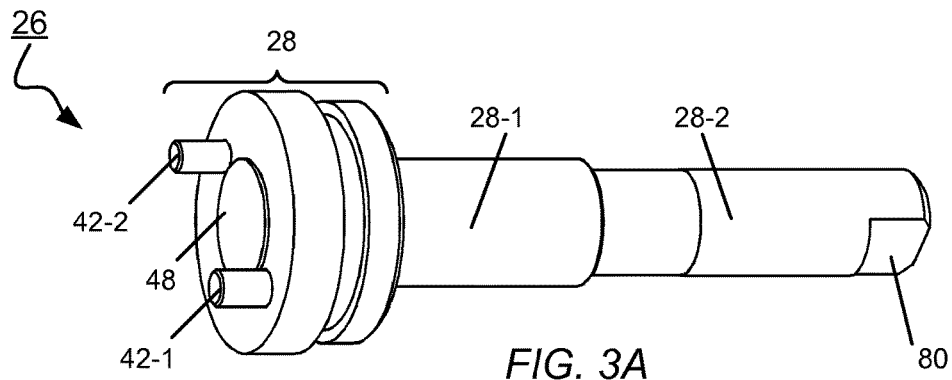
FIG. 3A is side view of an embodiment of a drive shaft of the rotor assembly.

FIG. 3A shows an isometric view of an embodiment of the rotor assembly 22, including the head portion 28 of the drive shaft 26. The head portion 28 has a generally disk-like shape with the dowel pins 42-1, 42-2 (generally, 42) and the dais 48 extending from a surface thereof. The pins 42 are diametrically opposite of each other; that is, considering the pins 42 to be endpoints of an arc on the circumference of this circle having its center at the center of the dais 48, the arc defined by the pins is semicircular (i.e., 180 degrees). These pins 42 enable torque transfer, and thus, rotation of the rotor assembly 22 as the drive shaft 26 rotates about the rotational axis 62. In one embodiment, the pins 42 are equal in length and pin 42-1 has a larger diameter than pin 42-2. Having one pin larger than the other pin provides a keying feature that ensures only one orientation by which the head portion 28 can couple to the rotor 24. Corresponding through-holes in the rotor 24 slideably receive the pins 42 in order to mount and align the rotor 24 relative to the drive shaft 26.

Figure 3B:
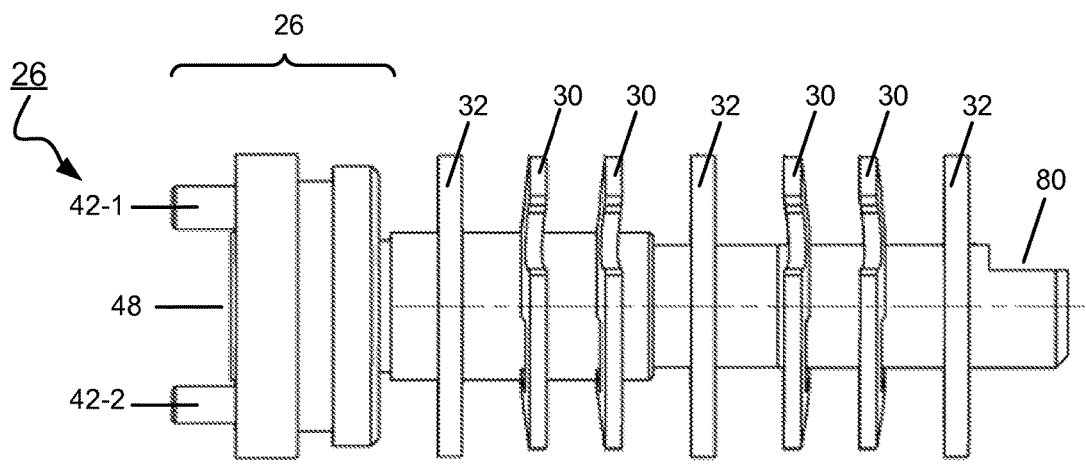
FIG. 3B is a side view of the drive shaft with springs about the drive shaft stem.

Also shown, the drive shaft 26 has a first portion 26-1 (adjacent the head portion 28) with a greater diameter than a second portion 26-2. At the end of the drive shaft 26 is a notch 80, sized to fit closely into the opening 50 (FIG. 1C) of the drive shaft clamp 16. FIG. 3B shows the rotor assembly 22 with the various springs 30 (here, e.g., clover springs) and washers 32 slipped over the drive shaft 26 (and uncompressed). For each set of two, the concave sides of the two clover springs 30 face the same direction. In addition, the concave sides of the two clover springs 30 in each set face in the direction of the concave sides of the two clover springs 30 in the other set. Preferably, the two springs in each set are in alignment with each other during assembly, although the two sets need not be in alignment with each other.

Figure 3C:
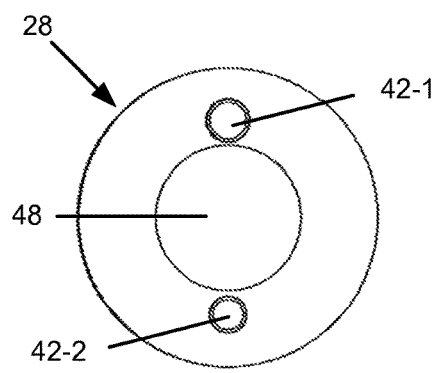
FIG. 3C is a top view of the drive shaft from the end with the pins.

FIG. 3C shows an end view of the leading face of the head portion 28 with the two pins 42-1, 42-2 and centrally located dais 48. In one embodiment, each pin 42 extends approximately 0.16 inches from a surface of the head portion 28, pin 42-1 having an approximately 0.109 inch diameter, pin 42-2 having an approximately 0.093 inch diameter, and the centers of the pins being 0.500 inches apart, with each pin being 0.250 inches from the center of the dais 48. In addition, in this embodiment, the dais 48 is raised approximately 0.012 inches from the surface of the head portion 28. Other pin sizes and locations can be employed without departing from the principles described herein.

FIG. 4A shows an isometric view of the disk-like shaped rotor 24 with a set of rotor grooves 90 disposed centrally on the contact surface 44 of the rotor 24. The length and position of the grooves 90 in the rotor surface 44 align the grooves 90 for coupling to various ports 70 of the stator 12 to other ports 70 of the stator 12 when the rotor 24 and stator 12 are in particular rotational alignments. In this embodiment, there are three rotor grooves (the rotor shear valve assembly being configured as an injection valve). Other embodiments can have one, two, or more than three rotor grooves, for use in other types of valves, such as vent valves and column manager valves.

In addition, the rotor 24 has two diametrically opposite openings 92-1, 92-2 (corresponding to the two pins of the drive shaft). The opening 92-1, referred to as a mating hole, is adapted to receive the smaller pin 42-2 of the rotor assembly 22 closely with tight tolerance. In one embodiment, the mating hole 92-1 has a diameter of approximately 0.095 inches for closely receiving the 0.093 diameter embodiment of the smaller pin 42-2. The opening 92-2 is an elliptically shaped slot adapted to receive the larger pin 42-1 of the two pins, with a greater measure of tolerance along the direction of the major axis of the slot than along the minor axis. In one embodiment, the minor axis of the slot 92-2 is approximately 0.110 inches wide for receiving the 0.109 diameter embodiment of the larger pin 42-1. The rotor 24 can slide onto the pins 42 of the head portion 28 without pressing. The ends of the pins 42 within the holes 92 of the rotor are approximately flush with the contact surface 44 of the rotor.

FIG. 4B shows a top view of the rotor 24 with a cross-sectional line A-A bisecting the openings 92-1, 92-2 and center point 94 of the rotor and passing though the ends of two of the rotor grooves. The center point 94 is the center of rotation of the rotor 24. In one embodiment, the center point 94 has an approximately 0.008 inch diameter. Detail region 96 encircles the rotor grooves 90 and center point 94.

FIG. 4C shows a cross-section of the rotor 24 taken along the line A-A of FIG. 4B. In the cross-section, each opening 92-1, 92-2 extends entirely through the rotor 24. In addition, to provide a sense of scale, the center point 94 and rotor grooves 90 appear as dark dots immediately below the surface 44 of the rotor 24. Detail region 98 surrounds the center point 94 and the one of the rotor grooves 90.

Figure 4E:
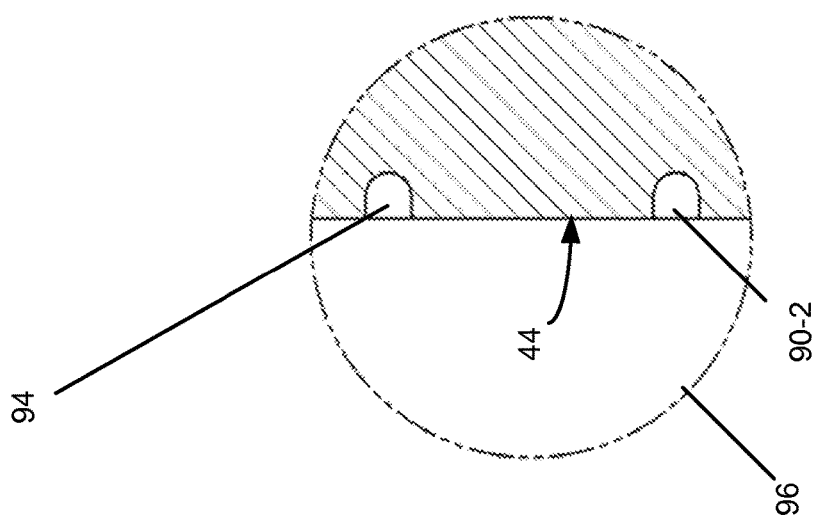
FIG. 4E is a view of detail region B of FIG. 4C.
Figure 4D:
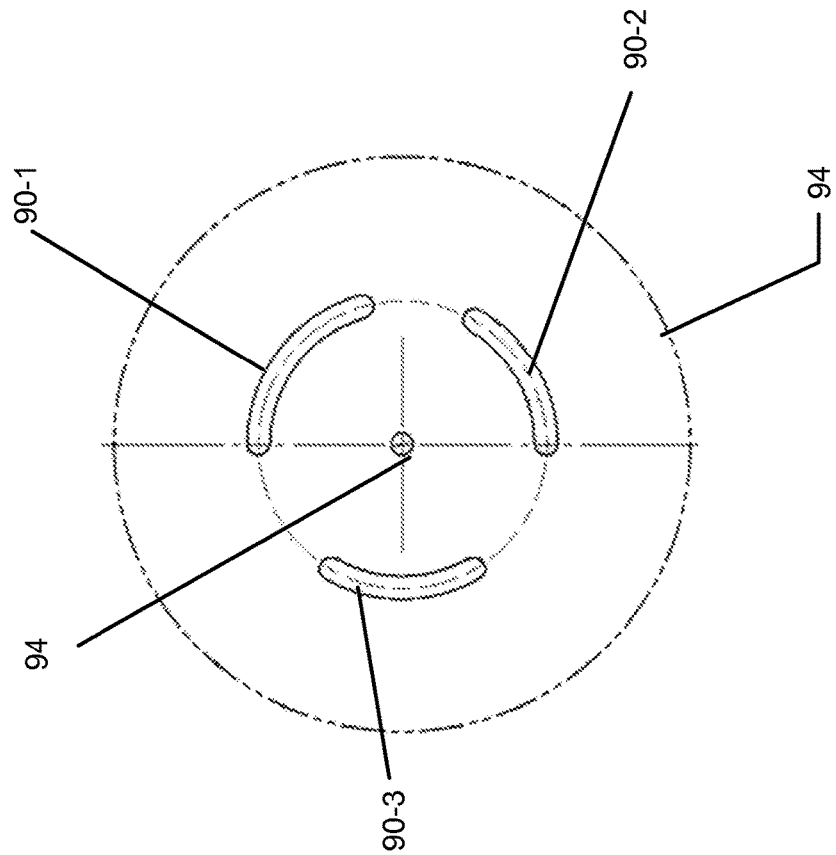
FIG. 4D is a view of detail region A in FIG. 4B.

FIG. 4D show a view of the detail region 96 of FIG. 4B, including the three rotor grooves 90-1, 90-2, and 90-3 (generally, 90). The rotor grooves 90 are arcuate in shape, and reside equidistant from the central point 94. In one embodiment, the rotor groove 90-1 forms an approximately 74 degree arc and rotor grooves 90-1 and 90-2 form 60 degree arcs, each groove being approximately 0.008 inches in width. FIG. 4E shows a view of detail region 98 of FIG. 4C, the rotor groove 90-3 (representative of all grooves 90) being a shallow channel and the center point being a shallow hemisphere formed in the surface 44 of the rotor 24. In one embodiment, the depths of the grooves 90 and center point 94 are approximately 0.008 inches.

Figure 5B:
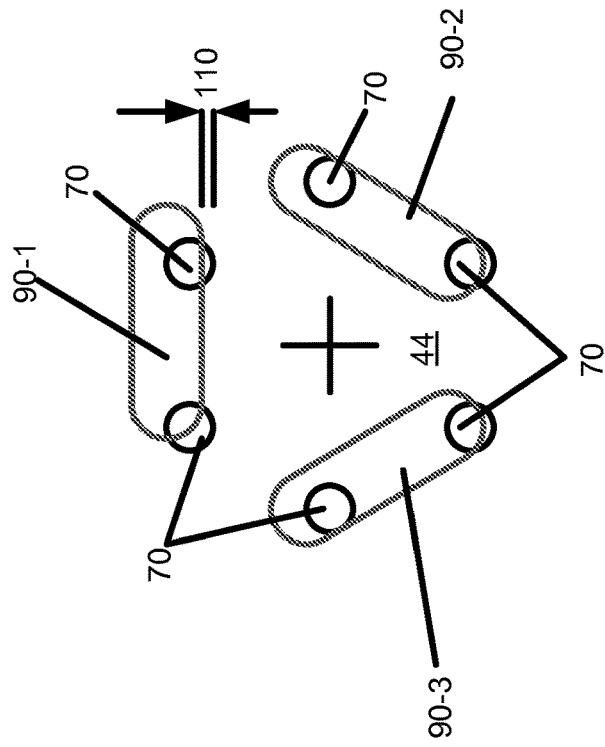
FIG. 5A and FIG. B are diagrams illustrating proper alignment and misalignment, respectively, between stator port openings and rotor grooves.
Figure 5A:
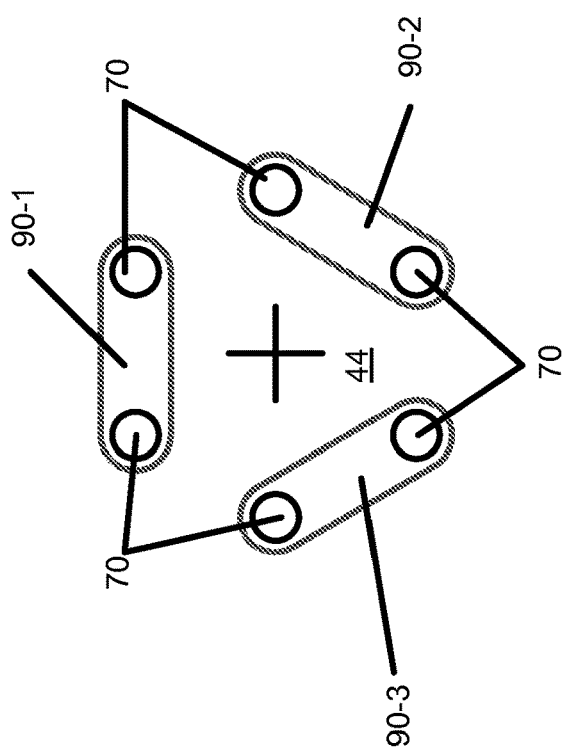

FIG. 5A and FIG. B are diagrams illustrating proper alignment and misalignment, respectively, between stator ports 70 and rotor grooves 90. In FIG. 5A, each rotor groove 90-1, 90-2, and 90-3 fully encircles two of the stator ports 70, thereby providing a fluidic channel between those stator ports. In FIG. 5B, a 0.002-inch misalignment 110 between the rotor 24 and the stator 12 can cause regions where the contact surface 44 of the rotor 24 covers a portion of a stator ports 70. Such misalignment leads to partial flow blockage, fluidic carryover, increased dispersion, uneven wear of the rotor and stator, and, consequently, reduced valve life. The tolerances of the two-pin draft shaft can improve rotor and stator alignment over conventional three-pin draft shafts.

Figure 6B:
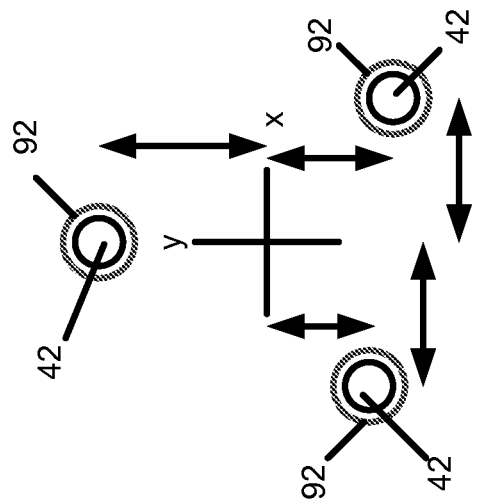
FIG. 6A and FIG. 6B are diagrams comparing the dimensioning of a two-pin drive shaft with that of a three-pin drive shaft.
Figure 6A:
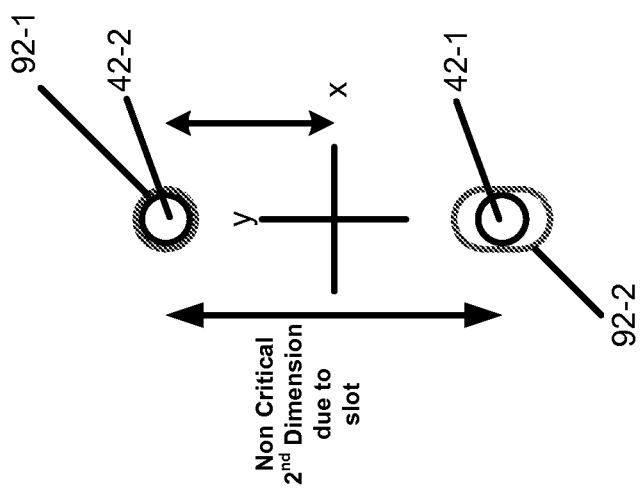

FIG. 6A and FIG. 6B are diagrams comparing the dimensioning of the two-pin drive shaft with that of a conventional three-pin drive shaft. For dimensioning the two-pin drive shaft, shown in FIG. 6A, the length of the slot 92-2 makes one of the two dimensions non-critical, in particular, the y-axis distance between the centers of the two pins 42. After the smaller pin 42-2 is in alignment with the mating hole 92-1, the length of the slot 92-2 provides a measure of tolerance for where the larger pin 42-1 can enter. In contrast, for the three-pin drive shaft shown in FIG. 6B, the vertical (y-axis) and horizontal (x-axis) distances between the centers of each pair of pins become critical dimensions that must be machined precisely to ensure alignment between the pins 42 and the holes 92. Thus, in comparison with the three-pin drive shaft, the two-pin drive shaft requires less through-hole clearance for the mating hole to receive the smaller pin, and leads to fewer critical position dimensions and less positional error.

Figure 7B:
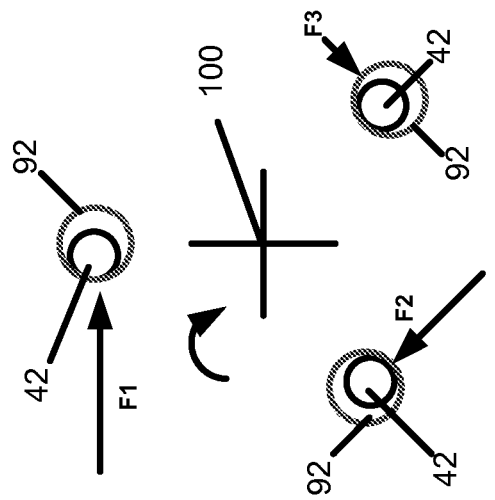
FIG. 7A and FIG. 7B are diagrams comparing the forces applied to the pins of a two-pin drive shaft with those applied to a three-pin drive shaft.
Figure 7A:
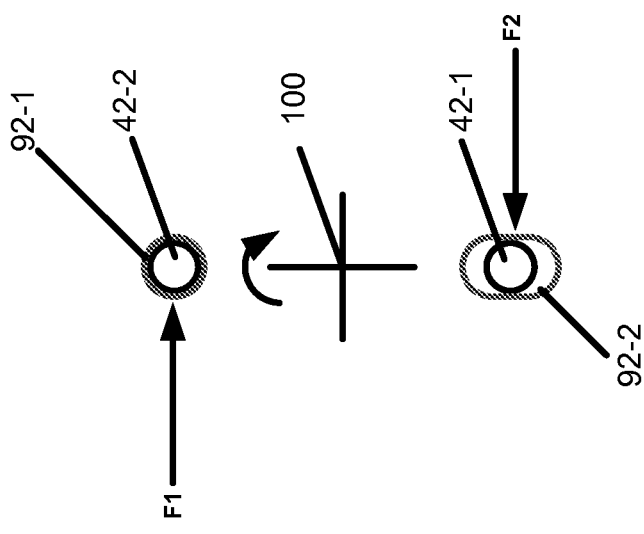

FIG. 7A and FIG. 7B are diagrams comparing the forces applied to the pins of the two-pin drive shaft with those applied to a three-pin drive shaft. For the two-pin drive shaft shown in FIG. 7A, the forces F1, F2 on the pins 42-1, 42-2, respectively, are diametrically opposite and equal, having a true "on-center" rotation effect. In contrast, for the three-pin drive shaft shown in FIG. 7B, only two of the three pins of the three-pin drive shaft bear most of the load because of positional errors; the force F3 does not act directly on the remaining pin. Consequently, the forces F1 and F2 applied to the other pins, in effect, carry the third pin. Thus, the forces acting upon the three pins are not equal for each pin, nor are the forces acting symmetrically about the center 100 of the rotor. This can lead to unequal rotor wear. Thus, in comparison with the three-pin drive shaft, the two-pin drive shaft leads to more uniform rotor wear and symmetrical internal rotor stresses, which leads to prolonged valve life.

The rotary shear valve assemblies described herein can be employed in a variety of high-pressure applications, examples of which include, but are not limited to, HPLC (High Performance Liquid Chromatography), UPLC (Ultra Performance Liquid Chromatography), analytical chemistry, and In-vitro Diagnostics (IVD). With respect to liquid chromatography applications, the rotary shear valve assemblies can be adapted for use as an injector valve assembly of a sample manger, a vent valve assembly of a pump system, and a column-manager valve assembly of a column manager.

While the invention has been shown and described with reference to specific preferred embodiments, it should be understood by those skilled in the art that various changes in form and detail may be made therein without departing from the spirit and scope of the invention as defined by the following claims. For example, in other embodiments, the two pins of the drive shaft and corresponding openings in the rotor may not be diametrically opposite each other; that is, the aforementioned arc defined by the pins (and corresponding rotor openings) can be other than 180 degrees.

What is claimed is:

1. A rotary shear valve assembly, comprising:
    a rotor assembly having a rotor and a drive shaft, the rotor having a substantially planar surface and the drive shaft having a head portion, the substantially planar surface having one or more rotor grooves, a first hole having a circular cross-section and a second hole opposite to the first hole along a diameter on the substantially planar surface defined between the first and second holes, the second hole having an elliptical cross-section which is not circular and wherein at least one of the rotor grooves intersects the diameter, the head portion having a first pin and a second pin, the first and second pins being disposed substantially diametrically opposite of each other on a line through a center of the head portion, the first pin having a diameter that is less than a diameter of the second pin, the first pin being mated with the first hole in the rotor and the second pin being mated with the second hole in the rotor, wherein the first hole in the rotor is sized to receive closely the first pin.

2. The rotary shear valve assembly of claim 1, further comprising:
a housing for the rotor assembly, one end of the drive shaft extending through an opening at a base of the housing; and
a clamp secured to the end of the drive shaft extending through the opening at the base of the housing.

3. The rotary shear valve assembly of claim 1 wherein the elliptical cross-section has a minor axis and wherein a dimension of the second hole along the minor axis is sized to closely receive the diameter of the second pin.

4. The rotary shear valve assembly of claim 1, further comprising a stator with a plurality of ports and a substantially planar surface with openings to the ports; and wherein the rotor assembly further comprises means for urging the rotor surface against the stator surface such that each rotor groove aligns with and provides a channel between two of the ports of the stator.

5. The rotary shear valve assembly of claim 4, wherein the means for urging includes a plurality of clover springs around the drive shaft, the clover springs being compressed to produce an axial force.

6. The rotary shear valve assembly of claim 4, wherein a seal formed between the surfaces of the rotor and the stator substantially prevents fluidic leakage up to 20,000 psi.

7. A rotary shear valve assembly, comprising:
a rotor assembly having a drive shaft and a rotor, the drive shaft having a head portion with only a first pin and a second pin each extending orthogonally from a distal surface of the head portion, the first pin having a smaller diameter than a diameter of the second pin, the rotor having a substantially planar surface, the substantially planar surface having one or more rotor grooves, a first hole having a circular cross-section and tightly receiving the first pin, and a second hole opposite to the first hole on a diameter on the substantially planar surface defined between the first and second holes, the second hole having an elliptical cross-section which is not circular and receiving the second pin, wherein at least one of the rotor grooves intersects the diameter.

8. The rotary shear valve assembly of claim 7, wherein the pins are disposed substantially diametrically opposite of each other on a line through a center of the head portion.

9. The rotary shear valve assembly of claim 7, further comprising:
a housing for the rotor assembly, one end of the drive shaft extending through an opening at a base of the housing; and
a clamp secured to the end of the drive shaft extending through the opening at the base of the housing.

10. The rotary shear valve assembly of claim 7, further comprising a stator with a plurality of ports and a substantially planar surface with openings to the ports; and wherein the rotor assembly further comprises means for urging the rotor surface against the stator surface such that each rotor groove aligns with and provides a fluidic channel between two of the stator openings.

11. The rotary shear valve assembly of claim 7 wherein the elliptical cross-section has a minor axis and wherein a dimension of the second hole along the minor axis is sized to closely receive the diameter of the second pin.

12. The rotary shear valve assembly of claim 10, wherein the means for urging includes a plurality of clover springs around the drive shaft and compressed to provide an axial force.

13. The rotary shear valve assembly of claim 12, wherein a seal formed between the surfaces of the rotor and the stator substantially prevents fluidic leakage up to 20,000 psi.

* * * * *